United States Patent
Flessner

(10) Patent No.: US 6,995,108 B1
(45) Date of Patent: Feb. 7, 2006

(54) METHOD FOR PRODUCING CATALYSTS BY ACID ACTIVATION

(75) Inventor: Uwe Flessner, München (DE)

(73) Assignee: Sud-Chemie AG, Munich (DE)

( * ) Notice: Subject to any disclaimer, the term of this patent is extended or adjusted under 35 U.S.C. 154(b) by 0 days.

(21) Appl. No.: 10/049,744

(22) PCT Filed: Jul. 9, 2000

(86) PCT No.: PCT/EP00/06507

§ 371 (c)(1),
(2), (4) Date: May 16, 2002

(87) PCT Pub. No.: WO01/08796

PCT Pub. Date: Feb. 8, 2001

(30) Foreign Application Priority Data

Jul. 30, 1999 (DE) ................................ 199 35 914

(51) Int. Cl.
*B01J 29/06* (2006.01)

(52) U.S. Cl. ............................. 502/81; 502/80; 502/84; 502/85

(58) Field of Classification Search .................. 502/80, 502/81, 84, 85
See application file for complete search history.

(56) References Cited

U.S. PATENT DOCUMENTS

| | | | |
|---|---|---|---|
| 2,464,127 A | 3/1949 | Gary | |
| 2,574,895 A | 11/1951 | Stecker | |
| 2,840,618 A | 6/1958 | Hecht | |
| 3,213,037 A | 10/1965 | Hodgkiss | |
| 3,452,051 A | 6/1969 | Sundholm | |
| 4,142,994 A | 3/1979 | Alafandi | |
| 4,193,454 A | 3/1980 | Goldstein | |
| 4,196,102 A * | 4/1980 | Inooka et al. ................. 502/62 |
| 4,278,820 A * | 7/1981 | Kametaka et al. ........... 568/678 |
| 4,329,257 A | 5/1982 | Sommer et al. | |
| RE31,036 E | 9/1982 | Inooka et al. | |
| RE31,038 E | 9/1982 | Inooka et al. | |
| RE31,039 E | 9/1982 | Inooka et al. | |
| 4,499,319 A | 2/1985 | Ballantine et al. | |
| 4,579,996 A | 4/1986 | Font Freide et al. | |
| 4,590,294 A | 5/1986 | Ballantine et al. | |
| 4,593,135 A * | 6/1986 | Gregory ..................... 585/446 |
| 4,692,425 A | 9/1987 | Schneider et al. | |
| 4,749,808 A | 6/1988 | Ballantine et al. | |
| 4,774,213 A | 9/1988 | Schneider et al. | |
| 4,866,020 A | 9/1989 | Atkins et al. | |
| 5,043,511 A | 8/1991 | Imai et al. | |
| 5,672,752 A | 9/1997 | Lai et al. | |
| 5,749,955 A * | 5/1998 | Shaked et al. ........ 106/287.17 |

FOREIGN PATENT DOCUMENTS

| | | | |
|---|---|---|---|
| EP | 352878 | | 1/1990 |
| EP | 0 925 829 | * | 6/1999 |
| JP | 53030996 | | 3/1978 |

OTHER PUBLICATIONS

Laszlo, et al., "Catalysis of Friesel- Crafts Alkylation by a Montmorillonite Doped with Transition-Metal Cations," *Helvetica Chimica Acta* vol. 70 (1987)

Cativiela, et al., "Clay-catalyzed Friedel-Crafts alkylation of anisole with dienes," *Applied Catalysis A: General* 123 (1995) 273-287.

* cited by examiner

*Primary Examiner*—Christina Johnson
(74) *Attorney, Agent, or Firm*—Scott R. Cox

(57) ABSTRACT

A process for producing catalysts by acid activation of phyllosilicates and coating with catalytically active metal ions wherein the acid activation is carried out in the presence of catalytically active metal ions. The solution which forms during acid activation together with the remaining solution which contains the excess, catalytically active cations are separated. The catalysts can be used for proton-catalyzed and Lewis acid-catalyzed reactions, especially for conversion of higher olefins with aromatic hydroxy compounds and amines, for esterification and dehydration reactions and for purification of aromatics.

6 Claims, No Drawings

METHOD FOR PRODUCING CATALYSTS BY ACID ACTIVATION

The invention relates to a process for producing catalysts by acid activation of phyllosilicates and modification with catalytically active metal ions.

Catalysts based on phyllosilicates, for example, clays, are used in many technical reactions. But naturally occurring clays, such as for example montmorillonite, kaolin, or attapulgite, in part have overly low activities. For this reason the clays for producing catalysts are often activated by treatment with acid. On the one hand, pure covering with for example sulfuric acid and, on the other hand, activation by extraction of the raw clay with acid, generally sulfuric or hydrochloric acid, can be done.

Thus, according to U.S. Pat. No. 3,452,056 an acid-covered montmorillonite catalyst (KSF/0) is used for alkylation of diphenylamine. According U.S. Pat. No. 5,672,752 an acid-extracted montmorillonite is used for the same reaction. Catalysts of this type are available under the commercial name Retrol, Fulcat and K10. According to U.S. Pat. No. 5,043,511, as a replacement for corrosive homogeneous catalysts, for example $AlCl_3$ or $BCl_3$, heterogeneous catalysts are used which are produced by coextrusion of clays with two different metal salts and thermal treatment at temperatures from 300° C. to 800° C. Products produced in this way are used as catalysts for alkylation of, for example, benzene with olefins.

But these modified clays also have disadvantages, for example, rapid deactivation or a complex production process, and there have been many efforts to eliminate these defects. Thus, U.S. Pat. No. 2,464,127 reports on a two-stage process with the object of obtaining amounts of iron as small as possible in the end product of acid activation of montmorillonite. According U.S. Pat. No. 2,574,895, some of the salts extracted in acid treatment are precipitated again on the montmorillonite-containing material, reducing reagents which are intended to prevent the iron from settling in the precipitation process being used. The effort to increase the service life of the resulting catalysts by reduced coke formation is common to both applications.

DE-A-1 271 682 describes a process for activation of montmorillonites by acid extraction in the presence of inert organic liquid compounds. Strong acids, such as for example hydrochloric or sulfuric acid, are used for acid activation. Due to the presence of organic components during decomposition of the clay by acid, the lattice distances of the resulting montmorillonite catalyst are increased, by which more catalyst centers become accessible to the substrate. The catalysts according to DE-A-1 271 682 are used for alkylation of phenolic compounds.

Other methods of activation are described in EP-A-352 878. In this case an untreated clay is covered by impregnation with, for example, zinc salts, copper salts or nickel salts. Organic solvents of the metal salts are used. The solvent is removed by distillation after impregnation. According to EP-A-144 219 and EP-A-031 252 raw clays are activated by a similar impregnation technique or by ion exchange. In ion exchange the natural intercalate cations of the minerals, mainly sodium, calcium and magnesium, are replaced by catalytically active metals. The disadvantage in this process is that the catalysts produced have an overly low pore volume. This means that only the outer surface is accessible to the substrates. Most of the inner surfaces of the catalysts are, however, not accessible. Thus, a large part of the possible activity remains unused.

To overcome this disadvantage, Laszlo in Helvetica Chimica Acta 70 (1987) 577 describes subsequent metal ion activation of already acid-activated montmorillonites. Thus, the commercially available catalyst K10 which is rich in pores and which is produced by acid activation of bentonite is modified by ion exchange with various metal salts. To do this the K10 present as a powder in a methanolic slurry is treated with solutions of the metal salts for several hours. The amount of metal ions used is computed such that they are present in a roughly 30- to 40-fold excess relative to the ion exchange capacity of the K10. Then the mixture is separated by filtration and the catalyst is washed free of salts and then dried. Especially good effects are achieved by ion exchange with aluminum salts and titanium salts. Replacement with iron salts leads to improved reactivity of the catalyst only in a few cases.

A similar process is also used by Cativiela in Appl. Cat. A 123 (1995) 273. Cativiela calcinates the catalysts additionally at temperatures around 500° C. in order to reduce the Bronsted activity. In this publication good activities are achieved especially with cerium salts. Replacement with iron ions however does not show any special effects.

The process used in these activation methods has at least two disadvantages. On the one hand, the process consists of two component processes which are independent of one another, specifically the acid activation of raw clays and the subsequent ion exchange reaction. Secondly, the ion exchange reaction must be carried out at a high ion excess. This necessarily leads to highly burdened waste water flows. In addition, the amounts of wash water necessary to clean the initial product after acid activation and for washing after ion exchange are very large, so that large amounts of waste water are formed thereby.

EP-B 284 397 describes a process in which the clay to be activated by the ion exchange is replaced in an upstream step with lithium ions and then thermally treated. With the resulting intermediate product ion exchange is then carried out in a second process step. Metal ions which are preferably used for this purpose are aluminum ions. Li clays with replaced iron ions do not show any improved activity compared to the initial material.

The object of this invention was to produce catalysts which have been modified with metal ions, and simple process steps and small waste water flows were to be guaranteed.

The subject matter of the invention is thus a process for producing catalysts by acid activation of phyllosilicates and modification with catalytically active metal ions characterized in that the acid activation is carried out in the presence of catalytically active metal ions. The solution which is formed during acid activation together with the residual solution which contains the excess, catalytically active cations are then separated.

It has been surprisingly found that highly active catalysts can be obtained from the acid activation of phyllosilicates in the presence of activating ions. In doing so it is not necessary to carry out activation and ion exchange in separate process steps. In the process as claimed in the invention, unexpectedly small amounts of the catalytically active ions are necessary. This process reduces process costs, and reduces the environmental burden of the process to a minimum. In certain cases, as for example with activation with iron ions or aluminum ions, the spent liquors obtained can even be used as precipitation aids in the clean-up of municipal sewage. It has furthermore been ascertained that the metal ions used for modification are present in an especially high degree of activation so that the amount of metal ions present in the final product can be kept especially low.

The subject matter of the invention is also the use of catalysts obtained using the process as claimed in the invention for proton-catalyzed reactions, especially for conversion of higher olefins with aromatic hydroxy compounds and amines, for esterification and dehydration reactions as well as for purification of xylene and for Lewis acid-catalyzed reactions, such as for example alkylation of aromatics.

The invention is illustrated by the following examples.

EXAMPLE 1

Comparison Catalyst

A previously dried Bavarian montmorillonite-containing raw clay with an ion exchange capacity (IEC) of 80 mVal/100 g was decomposed by hydrochloric acid treatment.

To determine the ion exchange capacity (IEC), the phyllosilicate to be studied was dried over an time interval of 2 hours at 150° C. Then the dried material was reacted with an excess of aqueous 2N $NH_4Cl$ solution for one hour with reflux. After a holding time of 16 hours at room temperature it was filtered, whereupon the filter cake was washed, dried and ground and the $NH_4$ content in the phyllosilicate was determined by nitrogen determination (CHN analyzer from Leco). The proportion and type of exchanged metal ions was determined in the filtrate by ICP spectroscopy.

During decomposition, 90.3 g of raw clay with a water content of 16.9% by weight together with 250.7 g water and 87.5 mg of 30% hydrochloric acid were treated in a three-neck flask with a reflux condenser for 8 hours at boiling. Afterwards the mother liquor was separated from the product by filtration by means of a Buchner funnel and washed using demineralized water until chloride could no longer be detected in the wash water. The washed filter cake was dried at a temperature of 120° C. and then ground.

The product obtained in this way has a BET surface area of 253 m$^2$/g (according to DIN 66131) and a pore volume of 0.403 ml/g (determined by nitrogen adsorption and evaluation of the adsorption isotherms using the BJH method—E. P. Barret et al., J.Am.Chem.Soc. 73 (1951) 373). The pore distribution curve obtained from BJH derivation showed a Gaussian distribution with a maximum at 5.5 nm. The material contained among others the following exchangeable metal ions:

| | |
|---|---|
| $Fe^{3+}$ | 1.0 mVal/100 g |
| $Al^{3+}$ | 11.4 mVal/100 g |
| $Ce^{3+}$ | <0.1 mVal/100 g |

EXAMPLE 2

Iron-Containing Catalyst

A Bavarian montmorillonite-containing raw clay with an ion exchange capacity IEC of 92 mVal/100 g was activated analogously to Example 1. In addition to the reagents indicated in Example 1, iron chloride in the form of a concentrated FeCl$_3$ solution was added to the batch. The following were used for this batch:

| | |
|---|---|
| Raw clay (17.2% by weight H$_2$O) | 82.8 g |
| Water | 250.3 g |
| HCl (30%) | 50.0 g |
| FeCl$_3$ solution (2.5 mole Fe/kg) | 6.0 g |

The product obtained in this way had a BET surface area of 290 m$^2$/g and a pore volume of 0.338 ml/g. The peak of the pore distribution curve was at 4.6 nm. The amount of exchangeable $Fe^{3+}$ ions was 2.0 mVal/100 g.

EXAMPLE 3

Iron-Containing Catalyst

Example 2 was repeated using 18.0 g FeCl$_3$ solution:

The product obtained in this way had a BET surface area of 400 m$^2$/g and a BJH pore volume of 0.491 ml/g. The peak of the pore distribution curve was at 4.7 nm. The amount of exchangeable $Fe^{3+}$ ions was 8.0 mVal/100 g.

EXAMPLE 4

Aluminum-Containing Catalyst

Example 2 was repeated using 7.24 g AlCl$_3$*6H$_2$O.

The product obtained in this way had a BET surface area of 315 m$^2$/g and a BJH pore volume of 0.425 ml/g. The peak of the pore distribution curve was at 3.3 nm. The product contained 18.0 mVal/100 g exchangeable $Al^{3+}$.

EXAMPLE 5

Cerium-Containing Catalyst

A montmorillonite-containing raw clay from Turkey was dried to a water content of roughly 15% by weight and was ground. The material with a resulting water content of 13.1% by weight was activated as described in Example 1, the reaction mixture having been enriched with Ce(NO$_3$)$_3$*6H$_2$O. The following were used for this batch:

| | |
|---|---|
| Raw clay (13.1% by weight H$_2$O) | 86.3 g |
| Water | 254.6 g |
| HCl (30% by weight) | 62.5 g |
| Ce(NO$_3$)$_3$.H$_2$O | 13.03 g |

Analysis of the product yielded a BET surface area of 379 m$^2$/g and a BJH pore volume of 0.431 ml/g. The peak of the pore distribution curve was at 3.0 nm. The product contained 5.1 mVal/100 g exchangeable $Ce^{3+}$.

EXAMPLE 6

Reaction of Phenol with Nonene

The alkylation reaction, example 11 from DE-A-1 271 682 was reworked analogously. In a 1 liter three-neck flask equipped with a thermometer, a magnetic stirring mechanism and a reflux condenser, 252.5 g (2.0 mole) nonene, 235.3 g (2.5 mole) phenol and 5.0 g catalyst from Example 2 and Example 3 were heated to 90° C. After 3 hours reaction time, the catalyst was filtered off. The filtrate was fractionated using a 10 cm Vigreaux column. In the boiling range from 159° C. to 181° C. the alkylation product nonyl phenol was obtained.

As Table I shows, higher yields were achieved with the catalysts as claimed in the invention compared to the undoped catalyst (Example 1). The narrower boiling range for Fe-modified catalysts indicates a more uniform product spectrum and thus higher selectivity of the Fe-containing catalysts.

TABLE I

Alkylation of Phenol with Nonene

| Catalyst | Boiling range of product | Yield |
| --- | --- | --- |
| Example 1 | 160–180° C. | 35.3% |
| Example 2 | 165–175° C. | 38.7% |
| Example 3 | 173–175° C. | 41.2% |

EXAMPLE 7

Reaction of Diphenylamine with Nonene

In a 500 ml three-neck flask, 42.5 g (0.25 mole) diphenylamine were heated to roughly 150° C. and melted. Then 5.0 g catalyst and 44.2 g (0.35 mole) nonene were added to the melt. After a reaction time of 4 h, a further 41.6 g (0.33 mole) nonene were added, the reaction temperature of 150° C. having been maintained. After a reaction time of 8 h the reaction mixture was separated from the catalyst by filtration. The yield of dialkylated diphenylamine was determined by infrared spectroscopy using the following formula:

(%) dialkylate=[Log($ext@$ 820 cm$^{-1}$/$ext@$ 743 cm$^{-1}$) +1.141]/0.019;

$ext@$ extinction (absorbance) at the indicated wave number. In doing so it was considered that the adsorption peak at 820 cm$^{-1}$ corresponds to the dialkylated products, and the adsorption peak at 743 cm$^{-1}$ corresponds to the monoalkylated products. The reaction mixture was measured at a layer thickness of 0.025 mm to determine extinction.

Table II lists the determined yields of the reaction with various catalysts.

TABLE II

Alkylation of Diphenylamine with Nonene

| Catalyst | Yield of dinonyl-diphenylamine (%) |
| --- | --- |
| Example 1 | 27 |
| Example 3 | 40 |
| Example 4 | 37 |
| Example 5 | 35 |

The example confirms the improved activity of the catalysts as claimed in the invention in diphenylamine alkylation compared to the prior art.

EXAMPLE 8

Esterification of Acetic Acid and Ethanol

In a 250 ml three-neck flask with a thermometer, a magnetic stirring mechanism and a reflux condenser, 72.0 g acetic acid and 55.2 g ethanol were mixed. Roughly 0.5 g was removed from the mixture, and the acid content was determined by titration with 0.1N sodium hydroxide solution against phenolphthalein. The educt mixture was heated by means of an oil bath to 85° C. and after reaching the temperature, it was exposed to 1.26 g catalyst (relative to the dry substance). With the addition of the catalyst a stopwatch, which was used to determine the reaction time, was started. Every 30 minutes roughly 0.5 to 1 g of sample at a time was withdrawn using a pipette. The small amounts of catalyst entrained in the sampling did not significantly influence the progression of the reaction and titrimetric acid measurement. Table III shows the measured conversions after 30 and 60 minutes reaction time.

TABLE III

Esterification of Ethanol and Acetic Acid

| | Conversion after 30 min (%) | Conversion after 60 min (%) |
| --- | --- | --- |
| Example 1 | 10 | 13% |
| Example 2 | 20 | 28 |
| Example 4 | 27 | 34 |

EXAMPLE 9

Dehydration of Cyclohexanol

In a three-neck flask with an attached Vigreaux column and distillation bridge, 250 ml cyclohexanol together with 5 g powdered catalyst as described in Example 3 and Example 5 were caused to boil. The products, cyclohexene and water, which formed during the reaction were continuously removed from the reaction space via the distillation bridge. The condensed amounts of water and cyclohexene were recorded as a function of the reaction time. After roughly 200 ml cyclohexanol were reacted, 250 ml substrate was again added to the reaction vessel. This process was repeated three times without a significant decrease of the reaction rate being observed. The product formation rate for the catalyst according to Example 3 was 1.9 ml/min, for the catalyst according to Example 5 it was 1.7 ml/min.

The example confirms the consistently high reactivity of the catalysts for proton-catalyzed reactions.

EXAMPLE 10

Continuous Purification of Xylene

Some of the filter cake obtained after washing the product according to Example 5 was dried at 110° C. and carefully crushed. The 0.25 mm to 0.50 mm grain fraction was screened out of the fragments. Five milliliters of these fractional granulates was placed in a 10 ml tube reactor through which industrial xylene flowed continuously via a HPLC pump. The tube reactor was heated by a temperature-controlled oil bath to 175° C., this temperature being kept constant during the experiment. To prevent gas bubble formation at this temperature, a back pressure regulator which regulated the working pressure in the reactor constantly to 30 bar was installed between the reactor and the likewise installed sampling valves. A LHSV (liquid hourly space velocity) value of 12 h$^{-1}$ was set via the HPLC pump.

The industrial xylene used has a bromine index of 580 mg/100 g due to the unsaturated aliphatic compounds. These unsaturated compounds were reacted on the granulated catalyst presumably by a Lewis acid-catalyzed alkylation reaction such that after treatment of the raw material the bromine index dropped to values less than 2 mg/100 g. Over time, deactivation of the catalyst which allowed the bromine index of the treated xylene to rise again took place. After reaching a bromine index of 20 mg/100 g, exhaustion of the catalyst was defined. The amount of xylene converted during this running time is a direct measure of the catalyst activity. Using the granulated catalyst as shown in Example 5, a running time of 18 days was achieved, a total of 25.86 l xylene having been converted. In a comparison test with a commercially available catalyst, the Süd-Chemie product Tonsil® CO 630 G, a total running time of 12 days with a xylene throughput of 17.24 liters was achieved during this time.

The example confirms the clear improvement of catalyst activity compared to the prior art.

The invention claimed is:

1. A process for producing catalysts comprising
preparing a mixture of a phyllosilicate and an activating acid;
adding iron cations to the mixture of the phyllosilicate and the activating acid;
activating the phyllosilicate by use of the activating acid in the presence of the iron cations by boiling the mixture;
separating a solution formed during the acid activation which contains excess iron cations from the activated phyllosilicate to produce the catalysts.

2. The process of claim 1 wherein the phyllosilicates are selected from the group consisting of smectites, chlorites, illites, vermiculites of the serpentine-kaolin group and of the sepiolite-palygorskite group including montmorillonite, beidellite and nontronit.

3. The process of claim 1 wherein the acid activation is carried out in the presence of an earlier acid activation solution, which solution contains aluminum ions.

4. The process of claim 1 wherein the acid activation is carried out in the presence of an earlier acid activation solution, which solution contains aluminum and iron ions.

5. The process of claim 1 wherein the phyllosilicates after acid activation in the presence of catalytically active cations are washed, dried and calcined.

6. The process of claim 1 wherein the iron ions are added to the mixture of phyllosilicate and activating acid in the form of a solution.

* * * * *